(12) United States Patent
Haadem

(10) Patent No.: US 8,657,836 B2
(45) Date of Patent: Feb. 25, 2014

(54) DEVICE FOR TISSUE DAMAGE PROTECTION DURING CHILD DELIVERY

(75) Inventor: Knut Haadem, Helsingborg (SE)

(73) Assignee: Vernix Pharma A/S, Oslo (NO)

( * ) Notice: Subject to any disclaimer, the term of this patent is extended or adjusted under 35 U.S.C. 154(b) by 141 days.

(21) Appl. No.: 12/867,508

(22) PCT Filed: Feb. 13, 2009

(86) PCT No.: PCT/EP2009/051729
§ 371 (c)(1),
(2), (4) Date: Oct. 1, 2010

(87) PCT Pub. No.: WO2009/101186
PCT Pub. Date: Aug. 20, 2009

(65) Prior Publication Data
US 2011/0022056 A1 Jan. 27, 2011

Related U.S. Application Data

(60) Provisional application No. 61/029,085, filed on Feb. 15, 2008.

(30) Foreign Application Priority Data

Feb. 15, 2008 (SE) .................................. 0800357

(51) Int. Cl.
*A61B 17/42* (2006.01)

(52) U.S. Cl.
USPC .......................................................... 606/119

(58) Field of Classification Search
USPC ........................... 606/119, 121, 122; 600/184
See application file for complete search history.

(56) References Cited

U.S. PATENT DOCUMENTS

| 5,395,354 A | 3/1995 | Vancaillie | |
|---|---|---|---|
| 2008/0097472 A1* | 4/2008 | Agmon et al. | 606/119 |
| 2008/0135053 A1* | 6/2008 | Gruber et al. | 128/831 |
| 2009/0043169 A1* | 2/2009 | Trieu et al. | 600/220 |

FOREIGN PATENT DOCUMENTS

| FR | 1026870 A | 5/1953 |
|---|---|---|
| GB | 1127548 | 9/1968 |
| JP | 9-504707 A | 5/1997 |
| WO | 2007/131109 A2 | 11/2007 |
| WO | 2009/020660 A1 | 2/2009 |

* cited by examiner

*Primary Examiner* — Ryan Severson
*Assistant Examiner* — Jonathan W Miles
(74) *Attorney, Agent, or Firm* — Capitol City TechLaw

(57) ABSTRACT

The present invention provides a device that protects the tissue in the posterior part of the introitus vaginae, i.e. the commissura posterior. The origin of perineal tear starts here when the segment is stretched to double or triple its length during delivery of the head. Tears can be more extensive into the perineal body, continue into the anal sphincter and in worse cases even through the whole perineum into the anal canal. In use the device may protect against perineal tears of the posterior vaginal wall into the mucosa, perineal skin, muscles, even more profound down to the anal sphincter muscle and into the rectum and the rectal mucosa.

28 Claims, 13 Drawing Sheets

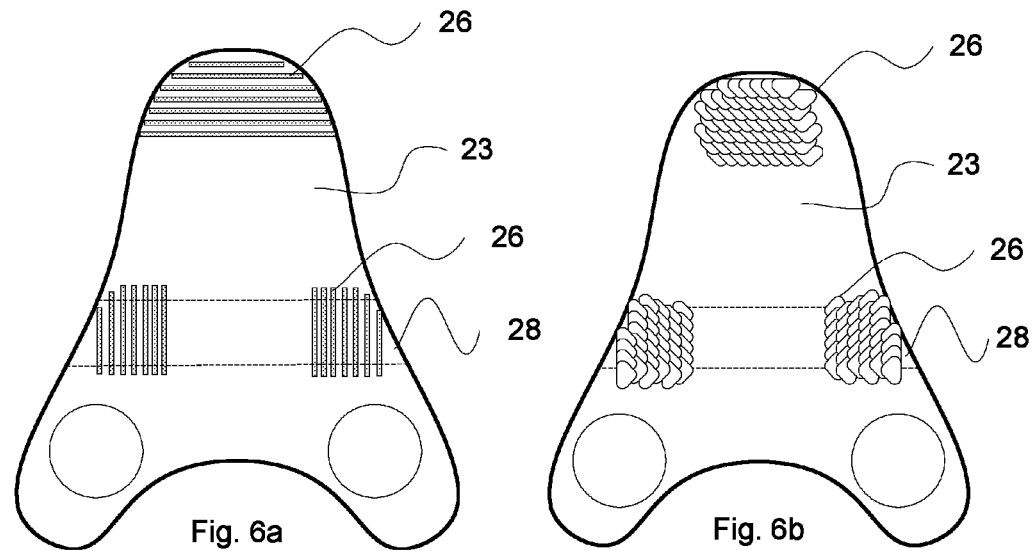
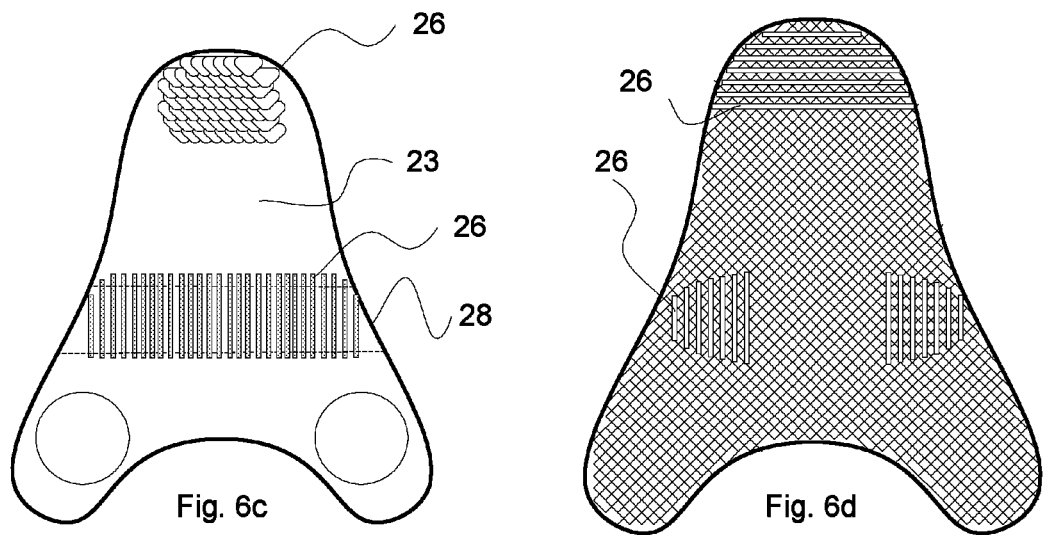

DEVICE FOR TISSUE DAMAGE PROTECTION DURING CHILD DELIVERY

FIELD OF THE INVENTION

This invention pertains in general to the field of child delivery. More particularly the invention relates to a device for protecting against tissue damage or tissue rupture during child delivery.

BACKGROUND OF THE INVENTION

Perineal tears causes much discomfort among women post partum, but even long term ailments can occur. Lacerations involving the anal sphincter function and anal canal are looked upon as more serious than the ones involving the mucosa and perineal body only, however all kinds of rupture give discomfort. The more extensive the rupture, the more troublesome are the complaints afterwards. Especially ruptures involving the anal sphincter muscles have been studied, since the frequency have increased the last two decades from 0.6% to approximately 4 to 8% varying between different obstetric departments. The long-term results of women with earlier anal sphincter ruptures having unfortunately shown that many are still suffering of anal sphincter incompetence. 50% of these women have persisting complaints with gas incontinence but also incontinence of liquid stool and in worst cases even formed stool. The reasons for this are many, but one is that the medium weight of the newborns has increased from 3.3 kg to 3.6 kg during the last 20 years. We know that baby weight and tears are related. It is therefore imperative to reduce the number of tears and give the perineum some protection especially with the future problems of increased baby weight in mind.

WO 2007/131109 A2 discloses a perianal support device that is configured to inhibit the formation and/or progression of tissue damage in the perianal region of the body. WO 2007/131109 A2 also discloses a method to apply the perianal support device to patients during childbirth to inhibit the formation and/or progression of tissue damage in the perianal region of the body. The device disclosed in WO 2007/131109 A2 comprises a construction having a rigid part (330, 340) intended to be in connection with the perianal region. Thus, the tissue in contact with the device is formed in accordance with the device by the pressure applied by the device. A further problem with the device of WO 2007/131109 A2 is that it does not reduce the risk of tissue ruptures originating from the posterior vaginal area, such as the lowest portion 9 of the vaginal opening, as it only protects the perianal area close to the anal sphincter. Moreover, the rigidness of the device provides for poor force distribution of the forces that arises during child delivery in the perineal area.

Delivery of the foetal head is when it passes through the introitus, i.e. the opening of the vagina. During this process minor or major spontaneous lacerations often occur, giving rise to postpartum discomfort and even long term effects as anal incontinence. The location of the rupture is usually located at the edge between the posterior wall of the vagina and the perineum (the skin between the vagina and rectum) the so-called commissura posterior. These ruptures can be classified in 4 different levels depending on the extension of the tear, where I is superficial and 4IV is an extensive tear into the rectum. When the rectum is involved the anal sphincter is usually injured as well.

Hence, an improved device, and method would be advantageous providing for reduced tissue damage of the mother during childbirth.

SUMMARY OF THE INVENTION

Accordingly, the present invention preferably seeks to mitigate, alleviate or eliminate one or more of the above-identified deficiencies in the art and disadvantages singly or in any combination and solves at least the above-mentioned problems by providing a device according to the appended patent claims.

According to an aspect of the invention a device for reducing tissue damage or ruptures during child delivery is provided. The device comprises a sheet having an upper side and a lower side, wherein at least a part of said lower side in use is configured to be in contact with a first area adjacent to the posterior part of the introitus vaginae or second area comprising the posterior part of the introitus vaginae, wherein said sheet is formable with said first or second area in use.

An object of the invention is to diminish the frequency of lacerations during delivery. This may be done in different ways; either by distributing the forces away from the areas liable for rupture or reinforce the same tissue during crowning of the foetal head i.e. when the head of the baby penetrates the vaginal opening. By doing this, the risk of perineal tears diminish and, subsequently, postpartum complaints. The force on the adjacent area may result in an increased pressure here, but this part is not so stretched and therefore not liable to tears.

BRIEF DESCRIPTION OF THE DRAWINGS

These and other aspects, features and advantages of which the invention is capable of will be apparent and elucidated from the following description of embodiments of the present invention, reference being made to the accompanying drawings, in which

FIGS. 6a to 6e illustrate a device according to an embodiment, respectively;

DESCRIPTION OF EMBODIMENTS

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

An object of the invention is to construct a device that protects the tissue in the posterior part of the introitus vaginae, i.e. the commissura posterior. The origin of perineal tear starts here when the segment is stretched to double or triple its length during delivery of the head. Tears can be more extensive into the perineal body, continue into the anal sphincter and in worse cases even through the whole perineum into the anal canal. In use the device may protect against perineal tears of the posterior vaginal wall into the mucosa, perineal skin, muscles, even more profound down to the anal sphincter muscle and into the rectum and the rectal mucosa. These ruptures are classified in four from I to IV grades depending of the extension of the lacerations.

Figure 1:
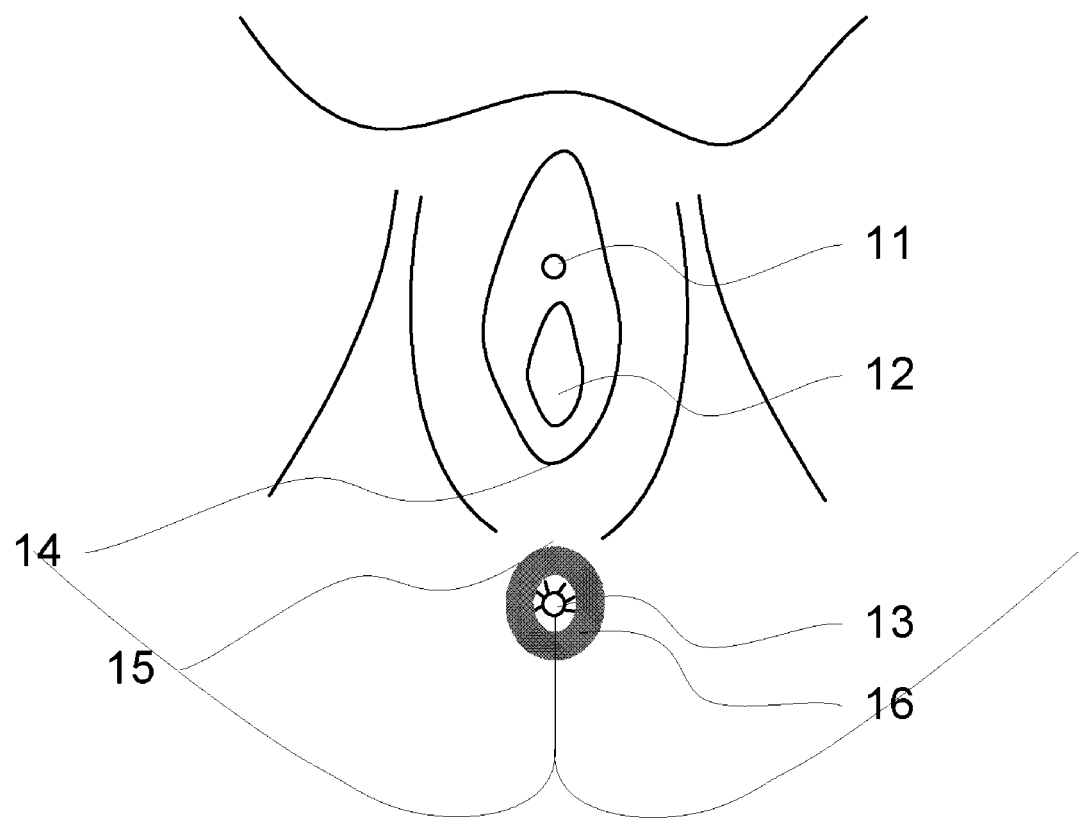
FIG. 1 is a schematic illustration of the posterior part of the introitus vaginae called the commisura posterior.

FIG. 1 is an illustration showing the posterior part of the introitus vagina, called the commisura posterior, which is the location where the tear of the rupture starts, during delivery of the head of the baby. FIG. 1 illustrates the urethral orifice 11, the vagina 12, the anal sphincter 13, commissura posterior 14, perineum 15, and anal sphincter muscle 16. The length of the posterior part of the introitus vagina is doubled or tripled depending of the head circumference and the presentation of the head (occiput anterior or vertex presentation for ex.). Reinforcement or protection of the tissue in the surroundings of commissura posterior would therefore reduce the risk of rupture and subsequently also of worst case scenario, when the anal sphincter muscle, perineal body and the rectal mucosa are involved. The present inventor has conceived that at least two main approaches could be used to protect this region from tears.

The following description focuses on embodiments of the present invention applicable to child delivery and in particular to a device for reducing tissue damage during child delivery.

Figure 2A:
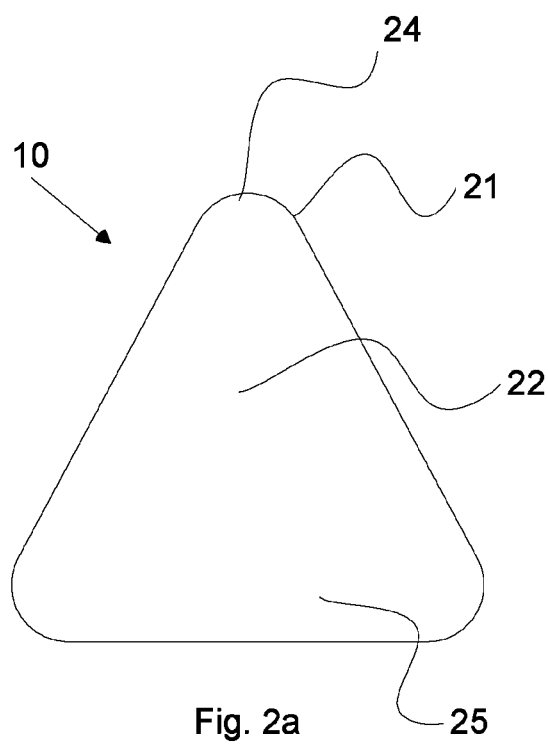
FIG. 2a is a top view showing a device according to an embodiment.

In an embodiment, according to FIG. 2a, a device 10 is provided. The device comprises a sheet of flexible material 21. The sheet flexible material has an upper side 22 with a smooth surface with low friction. In use the upper side is faced towards the baby's dorsal side such that the baby easily may slide over the upper side of the device. The flexible sheet also has a lower side 23 in use configured to be in contact with a first area adjacent to the posterior part of the introitus vaginae, such as the perineum, or second area comprising the posterior part of the introitus vaginae, such as the birth canal wall or the vaginal opening edge. The sheet is in use formable with the first or second area.

In an embodiment the first area is posterior wall of the lower vaginal canal.

In an embodiment the second area is the perineum.

In an embodiment the upper side of the flexible material is provided with a hydrophilic layer or coating (not shown) on its upper side. The hydrophilic layer provides for a smooth and slippery surface, facilitating the child during child birth to slide over the upper side 22.

In one embodiment, the hydrophilic layer or coating may be a hydrophilic polymer, such as poly-N-vinylpyrrolidone (PVP), PEO (polyethylene oxide), PEG (polyethylene glycol), or hyaluronan.

To improve the attachment of the hydrophilic polymers to the device, aryl ketones, such as benzophenone, may be used as a linker to covalently bind a hydrogel to a polymeric surface when activated by UV irradiation.

The polymer, to which the hydrophilic polymer is attached, may be silicone rubber, polypropylene (PP), polysulfone (PSF), polyvinylchloride (PVC), polystyrene (PS), polyethylene (PE), polycarbonate (PC), polymethylmethacrylate (PMMA), and polyurethane (PU).

In an embodiment the lower side is provided with an attachment means (not shown) for attaching the lower side 23 to the first or second area. The attachment means may e.g. comprise an adhesive, such as glue, e.g. tissue specific glue, creating an attachment of the lower side 23 of the device to the first or second area.

In an embodiment, the attachment means comprises a game for fixating the bottom side of the end section 25 or top section 24 of the device to the underlying tissue.

In an embodiment the adhesive is selected such that is may attach the lower side 23 of the device to the first or second area, while said first or second area is at least partly covered with body fluids such as, vaginal secretion.

The adhesive may be a smooth layer or coating, which may be compressed. Without limitations such layers or coatings may be selected from elastomers, such as silicone rubber, such as liquid silicone. By having a smooth surface, such as a surface without any protrusions or recessions, which surface may be compressed, as attachment mean, the device will be adopted to adhere to the first and/or second area by means of depression. Depression will be formed between the adhesive and the first and/or second area when the adhesive is pressed against the first and/second area. The presence of body fluids such as, vaginal secretion, will assist in the formation of depression as it will tighten the contact between the adhesive and the first and/second area.

In one embodiment, the smooth layer or coating, which may be compressed, may have circular, shallow recessions. Such recessions may act to increase the depression when the adhesive is pressed against the first and/second area.

In an embodiment the lower side is provided with an irregular surface that in use provides friction towards the posterior vaginal wall, thereby fixating the device during delivery. Without limitation, the lower side may be provided with a coating of cloth, to provide the device with means to provide friction.

Figure 2B:
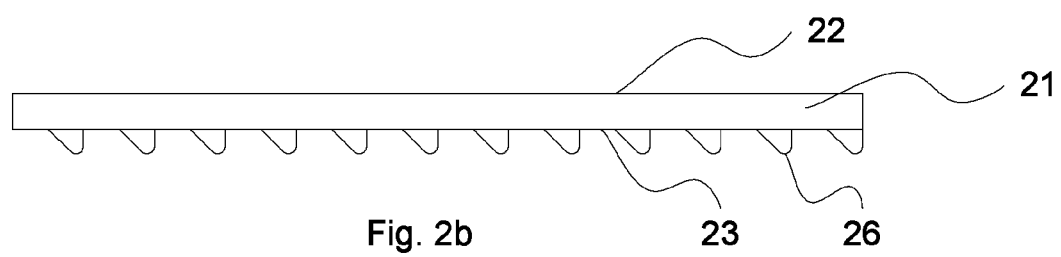
FIGS. 2b to 2d is a side view showing a device according to an embodiment, respectively.

FIG. 2b is a side view of the device and illustrates an embodiment in which the irregular surface is saw-shaped to provide friction with the posterior vaginal tissue. When placed in the vagina the device according to this embodiment become fixated toward the vaginal tissue by means of the saw-shaped irregularities and the force originating from the baby's head pressing the device downwards against the vaginal tissue.

Figure 2C:
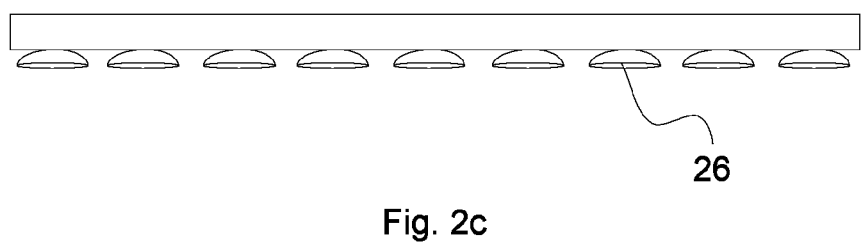

It should be appreciated that any irregular surface may be used to fix the device to the mucosa. Important is that the irregularities on the surface do not harm the mucosa. The irregular surface on the lower side of the device is especially important at the top section 24 of the device, where the placement under the baby head fixes the device by the pressure against the posterior vaginal wall. When the progress of the head proceeds, the rest of the device is fixed automatically as well. FIG. 2c illustrates another embodiment in which the lower side of the device is provided with small suction cups that adhere to the mucosa.

Figure 2D:
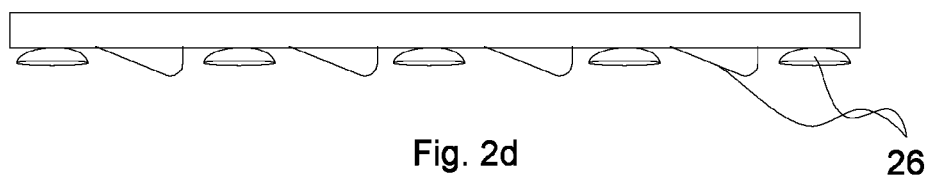

FIG. 2d is a side view showing the device wherein the irregular surface comprises a combination of suction cups and saw-shaped protrusions.

In another embodiment the lower side may comprise a lamellae pattern 26 according to FIG. 6a, fish shell pattern 26 such as is indicated in FIGS. 6b and 6c, or net structure according to FIG. 6d to prevent the device from gliding and providing friction towards the tissue to reduce tissue ruptures.

Accordingly, device according to some embodiments is configured to distribute the force originating from the baby's head to the commissura posterior during delivery to adjacent areas. In this way the force directed towards the anal sphincter 13 from commissura posterior 14 is distributed evenly along the vaginal wall and hence the load on the commissura posterior is drastically reduced.

The device may be applied in the posterior part of the vaginal opening called introitus, known as the commissura posterior. In a practical implementation the device may be put in place when the fetal head is some cm inside the introitus vaginae. Moreover, the device may be put between the posterior part of the fetal head and the posterior vaginal wall.

Figure 3:
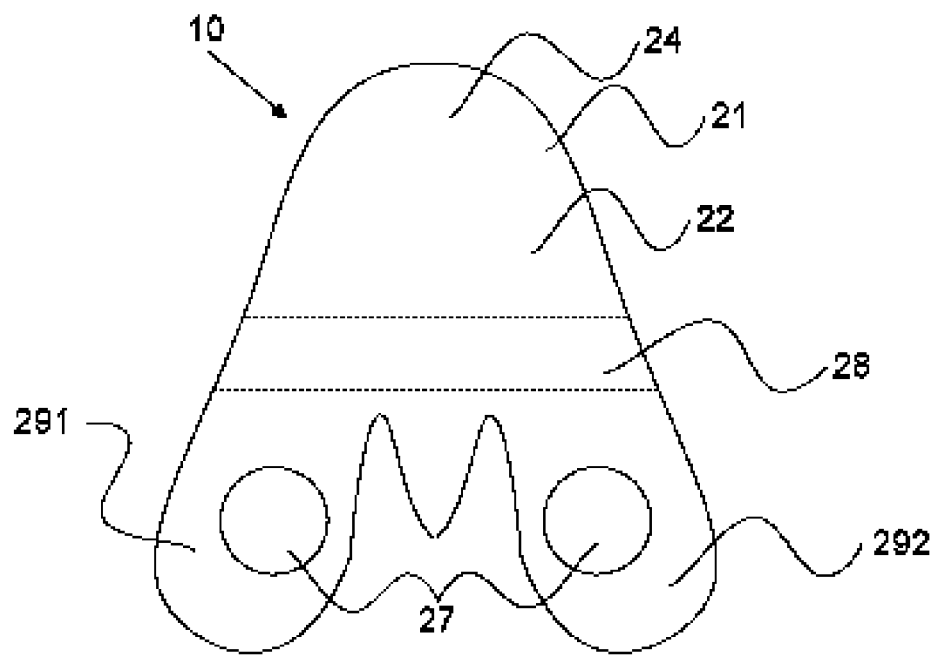
FIG. 3 is an illustration showing a device according to an embodiment.

In an embodiment, according to FIG. 3, the lower section 25 of the device is configured with an opening 27 in each end section 291 and 292, respectively, provided straight through the device. During use the attending health care personnel may use two fingers, such as the thumb and index finger, to manually decrease the tensions on the commisura posterior by pressing the openings towards each other. Moreover, the openings may be used for correction of location and insertion of the device. Another advantage of using a lower section design as in FIG. 3 is that as there is no material between the two end sections, the device is more easily bent over the edge at the vaginal opening. This is due to the fact that when bending the device around the edge at the vaginal opening the lower section of the device will extend or expand. Moreover, the upper part of the lower section closest to the middle section 28 will have to expand to a lesser degree than lower part of the lower section due to the fact that the vaginal opening is circularly shaped. Accordingly, by providing the device with end sections 291, 292 unnecessary material tension is avoided and a better fit is achieved. Moreover, this embodiment further reduces the tension forces on the commisura posterior.

In an embodiment the device comprises the end sections 291, 292 without openings provided.

Moreover, the device may be provided with a middle section 28 having increased flexibility for being able to be bent around commisura posterior while still being in contact with the tissue. In this way the device will be in contact with the vaginal opening edge thereby providing a force distribution to reduce the force on commisura posterior during childbirth.

Figure 4:
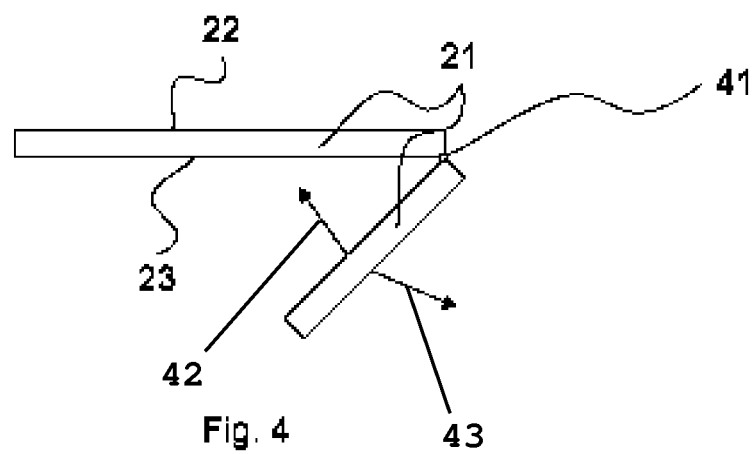
FIG. 4 is a side view of a device according to an embodiment.

In an embodiment the middle section 28 may be breakable e.g. using cuts provided in the upper side. In use, after placement of the device in the vagina, the middle section may be bent more easily based on the predefined cuts. FIG. 4 illustrates a side view of a device according to an embodiment wherein the device is bent using a cut provided in the upper side of the device. After bending the lower section of the device and the upper section of the device are connected at a joint 41. In FIG. 4 arrows 42 and 43 illustrates that the lower section may be rotated around the joint 41 for enabling a secure fit to the commisura posterior and the surrounding tissue.

Figure 5A:
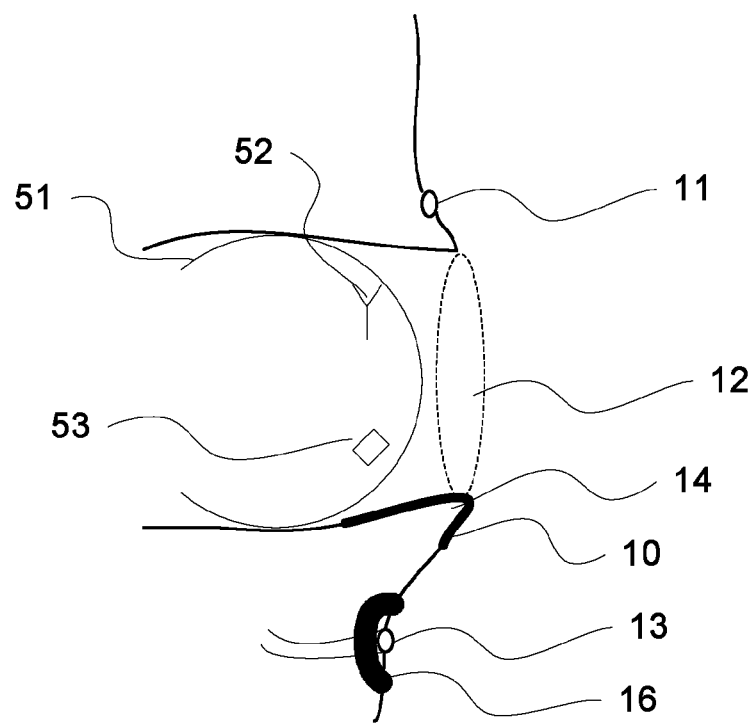
FIG. 5a is a side view showing a device in use according to an embodiment.
Figure 5B:
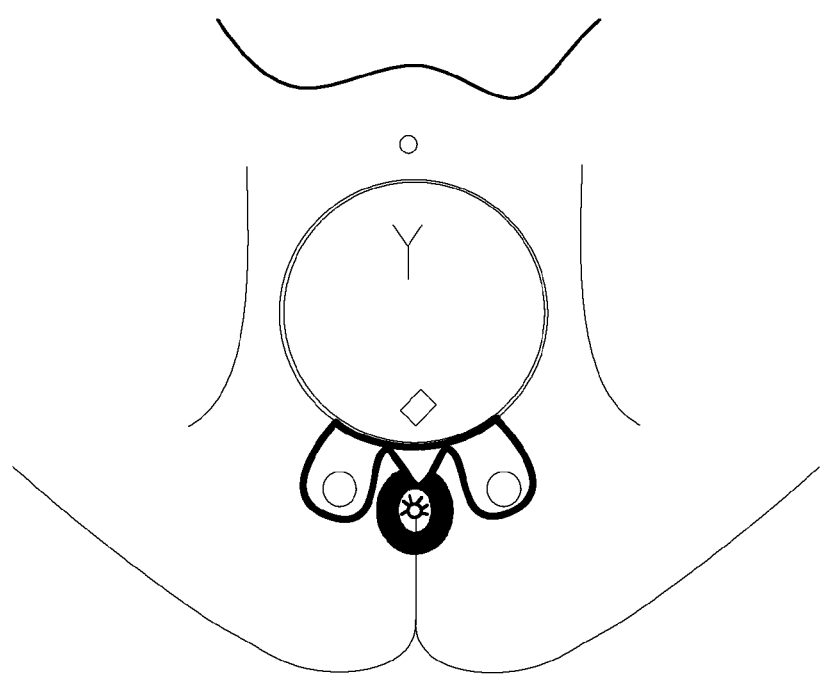
FIG. 5b is a front view showing a device in use according to an embodiment.

FIG. 5a illustrates a side view of the position of the device during childbirth. The baby's head 51 with the little fontanel 52 and large fontanel 53 will exert a force downwards towards the device 10 and protect the commissura posterior 14. FIG. 5b also illustrates the device in position during childbirth from a different angle.

Device Materials

In an embodiment the device is made of a flexible material. The flexible material of the device according may be elastic and is thus able to follow the transformation of the birth canal during delivery. This means that the sheet is formable. Accordingly, the device may change in shape throughout the child delivery process due to its elastic features. Thus, it may be extended along the vaginal opening edge as the vaginal opening expands during the child delivery counteracting the vaginal opening expansion forces at the posterior part of introitus vaginae by its intrinsic force features of returning to its equilibrium state, thereby providing force distribution around commisura posterior.

The device could be made of tissue/textiles that are adaptable to dynamic transformation of the vaginal wall.

The flexible material may e.g. polymeric material suitable to be used for medical applications. The flexible material may e.g. be polypropylene, polyethylene, polyurethane, polycarbonate, vinyl, polytetrafluoreten, silicon etc.

According to some embodiments the flexible material is transparent making possible a continuous inspection of the tissue. Textiles of different origin can be used.

The variety is numerous but the importance is that the substances give support to the tissue and that allergic reactions are not triggered. However, the material of the device is not limited to only polymeric materials, and accordingly any polymeric or non-polymeric such as metallic flexible material may be used, respectively or in combination.

The flexible material may be configured as a plate, with or without perforations. The flexible material may also be configured as lamellae, net, tissue or any combination.

In an embodiment each side may be of different origin, e.g. the lower side may consist of a net and the upper side a smooth surface plate. It should be appreciated as long as the device comprises one smooth side and one side providing friction any material(s) for accomplishing this may be used. The different solutions are numerous and the present invention is not limited to a certain choice of material(s), shape(s), size(s), or surface(s).

According to some embodiments the irregular surface may differ over the device area. FIGS. 6a to 6d illustrates different embodiments of the device.

FIG. 6a is a top view showing the device according to an embodiment configured with parallel lamellae 26 organized in the top section 24 perpendicular towards the direction of the birth canal and arranged parallel with the direction of the birth canal in the middle section 28. In this way, during child birth, the device will be prevented from sliding out of the vagina based on the lamellae in the top section, while the lamellae in the middle section will reduce the risk of tissue ruptures at the commissura posterior, by distribution of the forces to adjacent areas.

FIG. 6b is a top view of the device according to an embodiment wherein the irregular surface comprises a fish shell structure 26. The fish shell structure, when coming in contact with the tissue, will reduce the risk of tissue ruptures and at the same time becomes adhered to the tissue.

FIG. 6c is a top view of the device according to an embodiment wherein the irregular surface comprises a combination of fish shell structures and lamellae structures.

FIG. 6d is a top view of the device according to an embodiment wherein the irregular surface comprises a net structure with lamellae. The net structure will also provide a force distribution effect and thereby reduce the risk of tissue ruptures, while also become adhere to the tissue in contact.

In an embodiment at least the lower side 23 of the device is configured with a net structure that provides a suitable fit for the commissura posterior, covering the angle between the vaginal wall and perineum, which is sharp and changing during the birth process. The net structure e.g. provided on the lower side of the device prevents the device from sliding. When the vagina is distended due to the passage of the baby the net increases tissue resistance and reduced risk for tears. The net is simultaneously transformed and shortened and the net covers also the commissura posterior and some cm of the perineum, therefore pulling the posterior part of the vaginal opening backwards and facilitate the delivery of the head. The side of the net turning to the baby is smooth, easing the passage. The net size may be varied depending on the anatomical variations and the size of the head.

In an embodiment the irregular surface comprises a perforated material enabling the tissue to fill the perforations. This provides the same force distribution effect as mentioned above, and the friction between the device and the tissue will be increased.

Using a net structure, when the head progress through the birth canal vaginal wall, distension occurs and the distance between the lamellae placed at the vaginal wall beforehand increase. However, as the lamellas are tied together with elastic strings and placed at the vaginal wall with surface that adheres to the mucosa, this subsequently increases the tissue resistance.

The shape of the device may differ from embodiment to embodiment. In an embodiment the device has a triangular shape as is illustrated in FIG. 2 with an upper section placed under the head of the baby as demonstrated in the figure. The lower section of the device may be provided with end sections e.g. formed as two distinct half circles (placed on perineum) to indicate placement of the fingers for perineal support during delivery of the head.

Figure 6E:
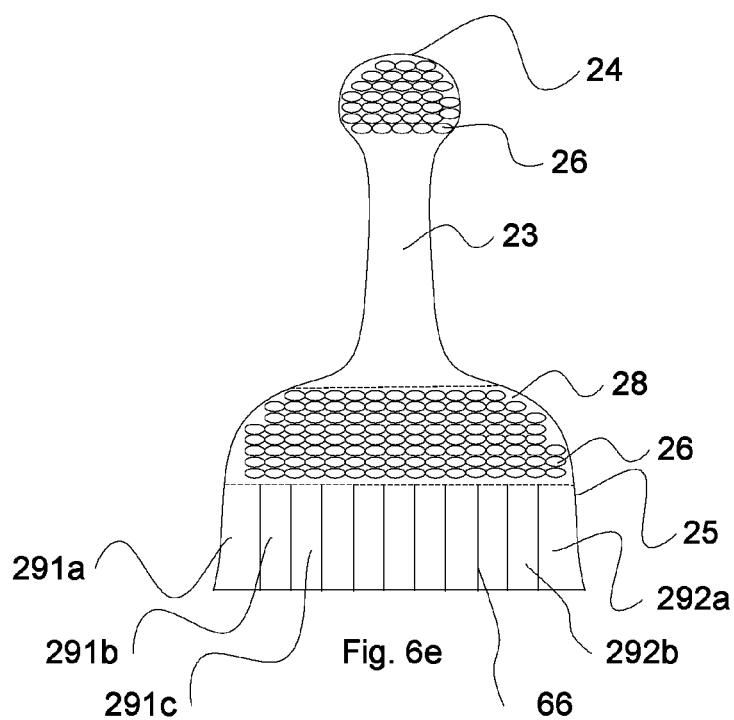

FIG. 6e is a top view of the device according to an embodiment. In FIG. 6e the top section 24 comprises a head-shaped body with a neck having smaller width than the head-shaped body and the middle section 28, providing a slim structure with a minimal amount of material. This construction may be advantageous when the anatomical size of the birth canal is limited. In this way, the birth canal will not have to extend in the same degree e.g. as compared to using a device according to FIG. 2.

The device according to FIG. 6e is provided with suction cups to enable the force distribution effect. Moreover the device may also comprise several end sections 291a, 291b, 291c, 292a, 292b, etc, each being separated from the others e.g. by means of a cut 66. The lower section construction according to FIG. 6e provides for the advantage that as midwifes commonly presses their hand towards perineum when the child is about to be delivered, this will increase the force distribution effect.

The device according to some embodiments is shaped to protect the outer part of the vagina and some cm beyond the commissura posterior of the perineum. FIG. 2 illustrates a device shape according to an embodiment. However, depending on anatomical differences between patients other shapes are equally possible to use. The passage of the head may proceed since the device is thin and does not interfere with the progress of the delivery. After delivery the device may be removed when its protective effect has been accomplished.

The device may be of different shapes as well as sizes and flexible materials.

The shape of the device may be made in different sizes depending of the anatomy of the birth canal and clinical results. For example, it may cover a distance, e.g. 4-6 cm of the commissura posterior a distance up on the posterior wall of the vagina as protecting the adjacent perineum. Size, shape, form and material can be combined in different combinations together or separately.

In an embodiment the device is thin, such as having a maximum thickness of 5 mm, such as 1 mm. The thickness of the device may differ over the device. In an embodiment the top section or middle section is 0.1 to 1 mm. In an embodiment the end section is over 1 mm, such as 2 mm. In this way the device does not interfere with passage of the head of the baby in the delivery canal.

In an embodiment the lower side 23 is provided with a coating (not shown) configured to attach said device to a material in contact with said lower side 23. For example, the coating may be configured such that when it comes in contact with the tissue of the first area or second area it attaches to the respective area, by means of chemical reactions. In some embodiments the coating may be used instead of the irregular surface for providing force distribution of the posterior part of the introitus vaginae. According to other embodiments a combination of coating and irregular surface may be used.

Figure 7A:
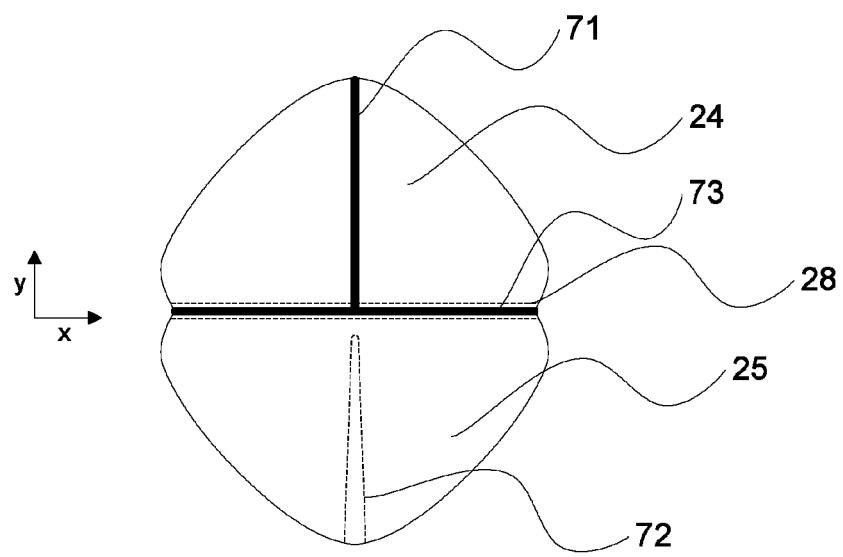
FIGS. 7a to 7b illustrate a device according to an embodiment, respectively.

In an embodiment, according to FIG. 7a, the top section 24 is provided with a reinforcement means, such as a reinforcement beam 71. The reinforcement beam is more rigid than the surrounding portion of the top section. A function of the reinforcement beam is to stabilize the device during child birth such that the device is prevented from being displaced or folded in use, when the child comes into contact with, and passes the device.

In an embodiment the reinforcement means does not extend all the way up to the edge of the top section as is indicated in FIG. 7a but instead may end before, i.e. at a distance from, the edge of the top section, whereby the edge of the top section remains softer than if the reinforcement means would have extended from the middle section and all the way to the end of the top section. Similarly, the reinforcement means may extend at a distance from middle section and to the edge of the top section or at a distance from the edge of the top section.

The reinforcement beam may be integrated into the top section 24 of the device such that the thickness of the device at the location of the reinforcement beam is essentially equal to the thickness of the top section 24 portion surrounding the reinforcement beam.

Figure 9:
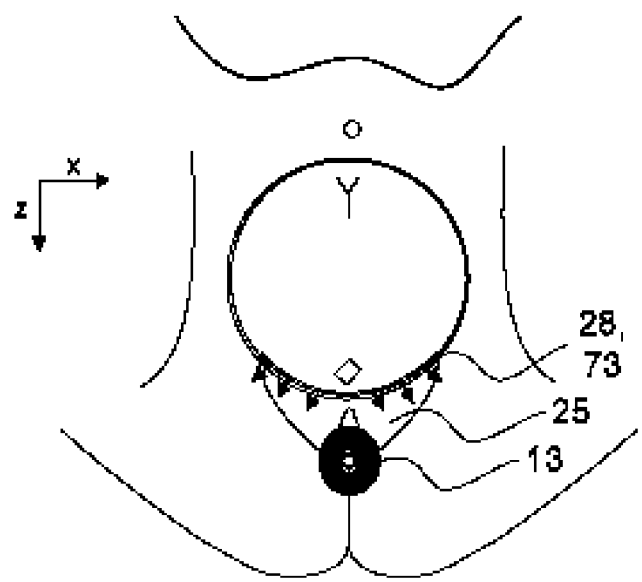
FIG. 9 illustrates a front view of a device according to an embodiment, in use.

In an embodiment the lower section 25 comprises a slit 72, dividing the lower section 25 into essentially two halves, i.e. end sections. The length of the slit may be varied, such as extending partly or fully from the edge of the lower section(s) to the middle section of the device. The function of the slit is to facilitate bending of the middle section 28, in use. FIG. 9 illustrates a device having said slit 72, in use, when the middle section 28 is bent along with the edge of the posterior part of introitus vaginae.

Figure 7B:
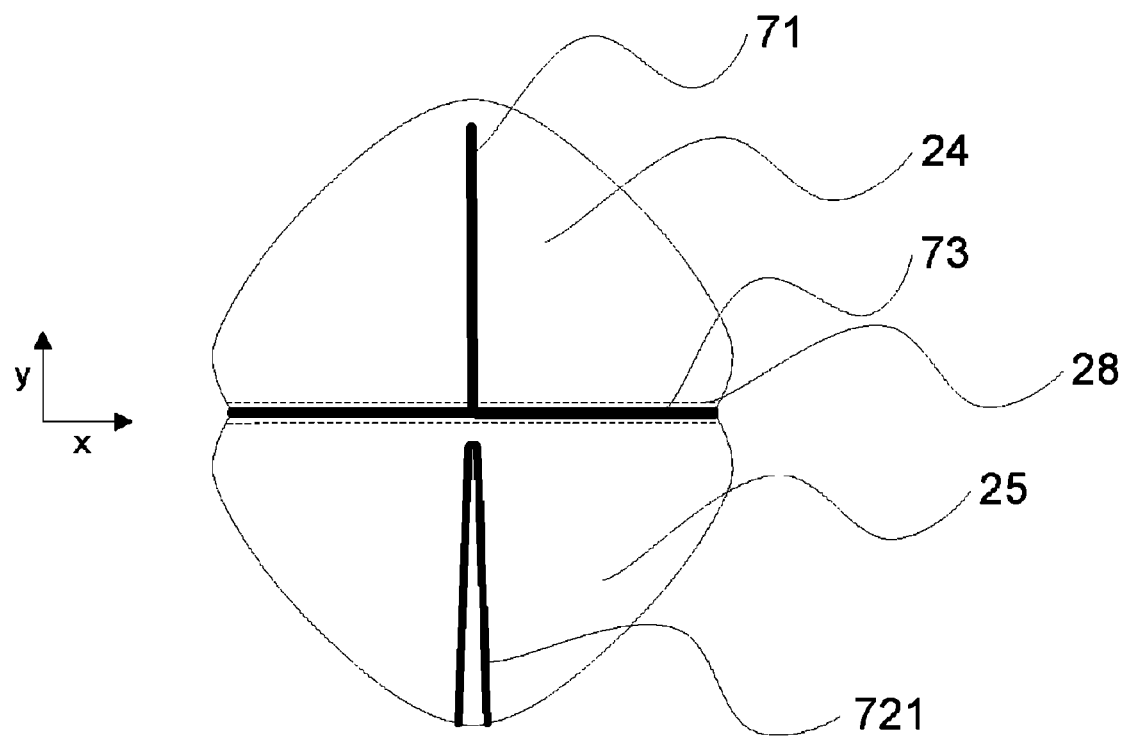

In an embodiment the middle section 28 comprises a reinforcement beam 73. The reinforcement beam may be provided in a straight shape, such as indicated in FIG. 7a, 7b, or in an arcuate shape. The arcuate shape may be provided such as to fit along the curvature of the vaginal opening edge. The reinforcement beam 73 is more rigid than its surrounding portions. When bent the reinforcement beam 73 due to its intrinsic character strives to return to its original configuration. Thus, when bending the reinforcement beam 73, due to the intrinsic character, passive forces, indicated by arrows in FIG. 9, counteract the bending. These passive forces contribute to the force distribution of the device during child delivery, since they indirectly act to keep the tissue, to which the middle section is in contact, together in conjunction with the attachment means or the irregular pattern provided on the lower side of the device.

The reinforcement beam 71 or 73 may be made of a material having a higher stiffness than the flexible material. Different materials may be used for reinforcement beam 71, and 73, respectively. However, the material of the reinforcement means having a higher stiffness than the flexible material may in fact comprise the same material as the flexible material, but having higher concentration or compactness, making the material of the reinforcement means stiffer than the flexible material.

In an embodiment an edge of the lower section along the slit is provided with reinforcement means. When both edges of the slit 72 is provided with a reinforcement means 721, e.g. integrally connected, as is indicated in FIG. 7b, the intrinsic forces of the reinforcement means strives to keep the edges on each side of the slit together thereby exerting a counterforce when the vaginal opening is expanding during child delivery. This counterforce also assists in reducing the risk of perineal tears or ruptures during the child delivery.

Figure 8A:
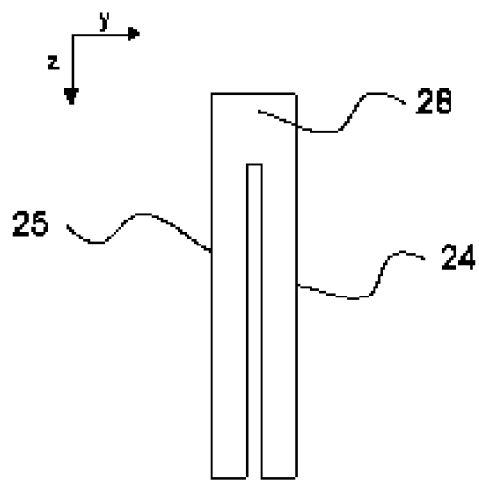
FIGS. 8a to 8c illustrate a device according to an embodiment, respectively.
Figure 8B:
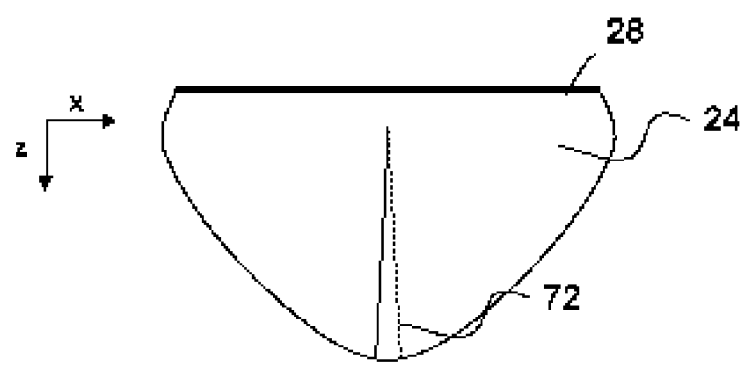
Figure 8C:
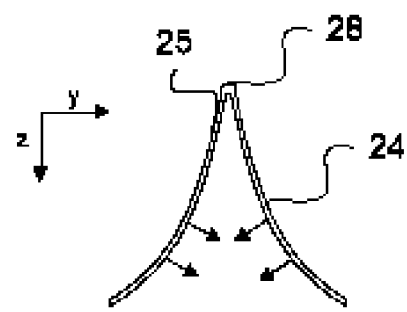

In an embodiment, according to FIG. 8a, the top section 24, and the lower section 25 both extends from the middle section 28 in essentially the same direction, forming a device having a U-shape form seen from the side in the y-z plane in its idle state. The base of the U-shape constitutes a reinforcement means. FIG. 8b illustrates a front view, in the x-z plane, of the device of FIG. 8a. Due to the intrinsic character of the device, it strives to return to its original idle U-shape configuration. The arrows in FIG. 8c indicate the intrinsic passive forces of the device, when bent. In use, when the top section 24 is placed in the posterior part of the introitus vaginae, and the end section 25 is placed outside the birth canal, the passive forces act to hold the underlying tissue together, thereby reducing the risk of tears or ruptures during the child delivery.

FIG. 9 illustrates the device according to an embodiment, in use. In FIG. 9, the arrows indicate the passive forces, due to the intrinsic character of the device, when the device is bent along the vaginal opening edge. The effect of the passive forces is that the underlying tissue is held together and stabilized, thereby reducing the risk of tears of ruptures during child delivery.

In an embodiment the area constituting the slit 72, i.e. the area between the end sections, which in use lie against the perineum is covered by a stretchable plastic membrane (not shown), protecting the baby to come in contact with the faecal content from the mother during delivery, which is otherwise often the case.

In an embodiment the flexible membrane is thinner than the end sections, such as to minimize the internal passive forces when it is extended. Thereby the middle section 28 is allowed to bend along with the curvature of the vaginal opening edge, while still protecting the child, as well as the birth canal from contamination by faecal content.

Figure 10:
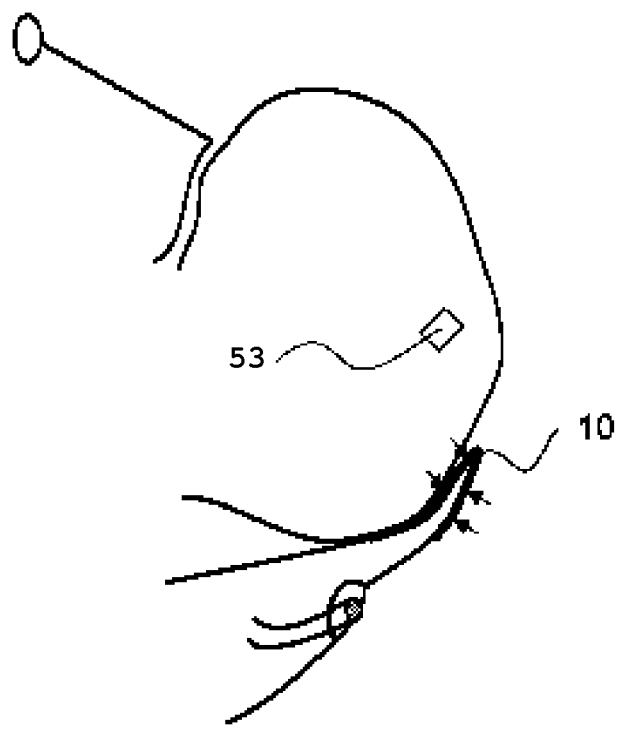
FIG. 10 illustrates a side view of a device according to an embodiment, in use.

By means of the intrinsic forces of the device, when the device is placed in the vaginal and perineal part in use, the device will exert the intrinsic forces onto the underlying tissue, thereby compressing and stabilizing the posterior vaginal wall and the perineum, in use. FIG. 10 is a cross sectional side view of the device in use, wherein the arrows indicate the at least some of the intrinsic forces of the device.

Figure 11:
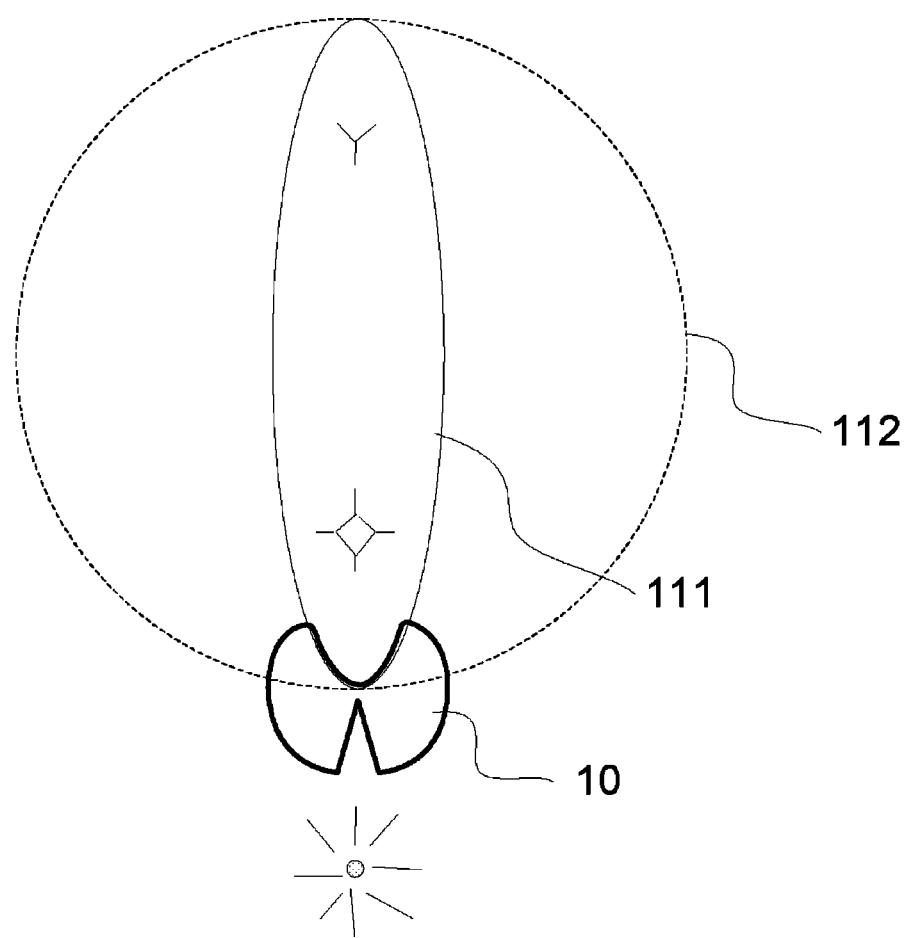
FIG. 11 illustrates a front view of a device according to an embodiment, in use.

FIG. 11 illustrates a front view of the device 10 according to some embodiments, in use, wherein the vaginal opening 111 in slightly open, and the head of the child behind the vaginal opening is indicated by a dashed line 112.

Reinforcement

Figure 12:
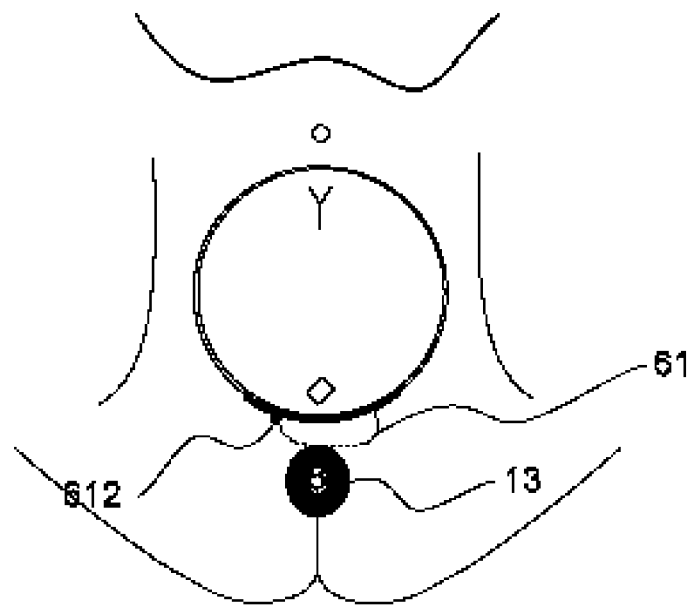
FIG. 12 is an illustration showing the device according to an embodiment being attached by means of a suture.

In an embodiment, according to FIG. 12, the device is configured to increase the resistance of the tissue in the area of commissura posterior by reinforcement, e.g. by means of increased friction between device and the commissura posterior and adjacent areas e.g. using an attachment means 61, such as an elastic suture, or a clamp, or that the surface of the device being in contact with the interior vaginal wall is configured to provide friction between the device and interior vaginal wall. In this way the elasticity of the mucosa and tissue in the posterior part of the introitus vagina may be reduced. Thereby, the stretching of the introitus is reduced.

Elastic sutures possess a quality of being extended, depending on the exposed force and there is a correlation between the extension of the suture and the force. These have the function of tissue reinforcement in the posterior region of the vaginal opening and reduced risk for tears going through the perineal body. The sutures are placed 0.5 to 1.5 cm inside the vaginal opening approximately 1 cm from the posterior midline both. The suture is fixed with movable buttons that keeps the suture in place, does not interfere with the passage of the baby and are easily identified for example with colors. The buttons can be of different sizes depending on required tissue support. The sutures can also be placed in the same vaginal location but set via the perineal skin before re-entering back into the counter-lateral side in the vagina and fixed. With this technique a part of the suture is outside at the perineum and can easily be cut and removed after the delivery. In case the suture is made through the perineal body, removal is easily done because of the anchoring buttons 612 that are grasped, lifted and cut. Local aesthesia is used before the stitches are placed. Clamps may after local anaesthesia be put on each side of the commissura posterior. The clamps may be connected with elastic strings to obtain resistance when the distension of tissue takes place. According to some embodiments a combination of sutures and clamps may be used. Accordingly, in this embodiment the commissura posterior is reinforced and the risk of tears will be reduced. In conjunction with the force distribution of the device the risk of tissue damage during childbirth will be significantly reduced.

Figure 13:
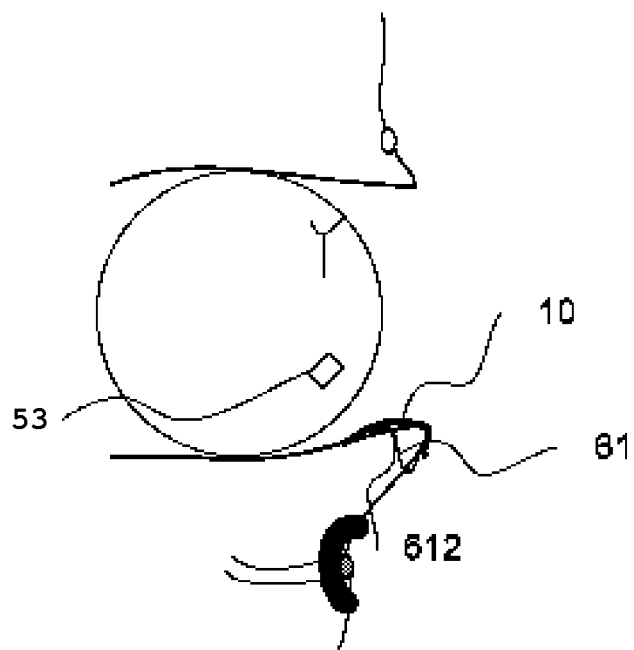
FIG. 13 is a side-view showing the device according to an embodiment being attached by means of a suture through perineum outside and back into the vagina on the opposite side.

FIG. 13 is a side view of a device in use attached to the tissue using an attachment means.

In a practical implementation the device according to some embodiments may be placed at a first distance inside the vaginal opening under the head posteriorly and the vaginal wall. In use at least some parts of the device will protect the nearby surroundings of the perineal area, such as at a second distance along the vaginal opening. The vaginal opening is now oval and changes form as the crowning proceeds to a circular shape, when the head penetrates the introitus. Due to the flexible material of the device it adapts its shape to the anatomical changes occurring during delivery. The first distance may e.g. be 1 to 3 cm, 6 to 8 cm or 1 to 10 cm inside the vaginal opening, depending i.a. on the given anatomical conditions. The second distance may e.g. be 1 to 2 cm, or 2 to 4 cm form the midline of the device, which second distance is defined by the end section(s), optionally in conjunction with the stretchable plastic membrane provided on the slit 72.

Figure 14A:
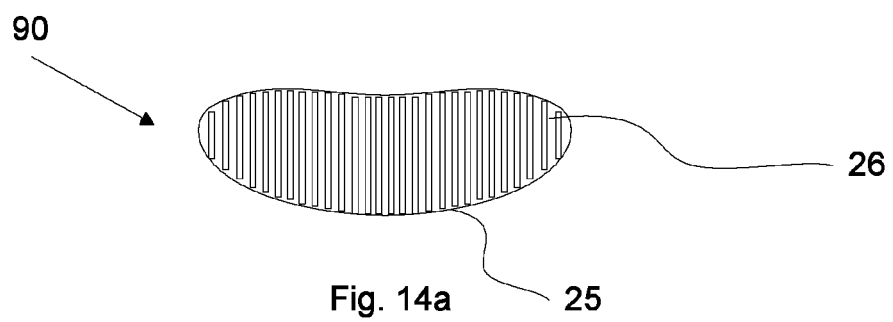
FIGS. 14a to 14c is a top view showing a device according to an embodiment, respectively.
Figure 14B:
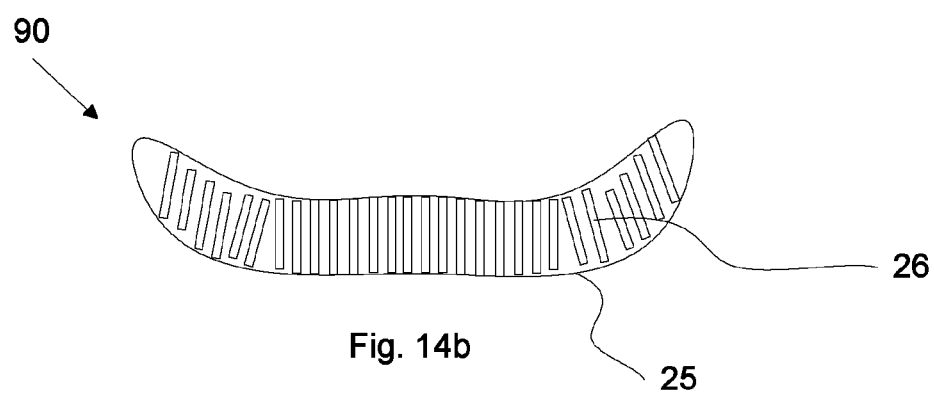
Figure 14C:
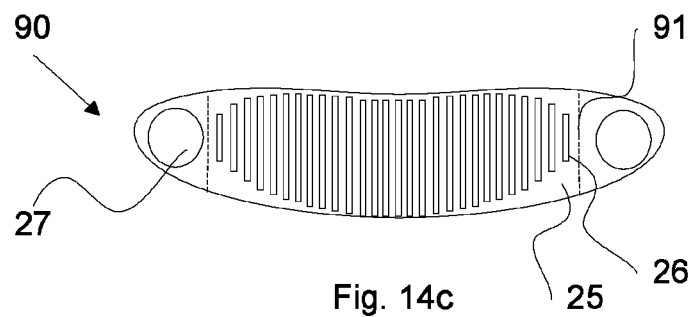

The device for reducing the tension of the tissue and tears during child delivery may be used separately, or in conjunction with other common child delivery devices FIGS. 14*a* to 14*c* illustrates embodiments of a device 90 wherein the top section and middle section according to earlier disclosed embodiments is absent and consequently the device 90 instead only comprises an end section 25 to be attached to the perineum or commisura posterior utilizing the attachment means or by applying manual pressure on the device towards the tissue, e.g. by hand. The device 90 may be provided any combination of irregular surfaces to improve the force distribution effect. In the device embodiments in FIGS. 14*a* to 14*c* the irregular surface comprises lamellae.

FIG. 14*a* illustrates a device in an idle position, i.e. an equilibrium state in which the device is not affected by external forces.

FIG. 14*b* illustrates the same device in an extended state due to external forces, such as the forces occurring from the dilatation of the birth canal during childbirth.

FIG. 14*c* illustrates a device to be attached via the attachment means wherein openings 27 are provided to enable manual operation in reducing the forces on the commisura posterior during childbirth. The device of FIG. 14*c* is provided with plication structures 91 for improving the manual operation of the openings during childbirth, and thereby improving the force distribution effect.

Figure 15:
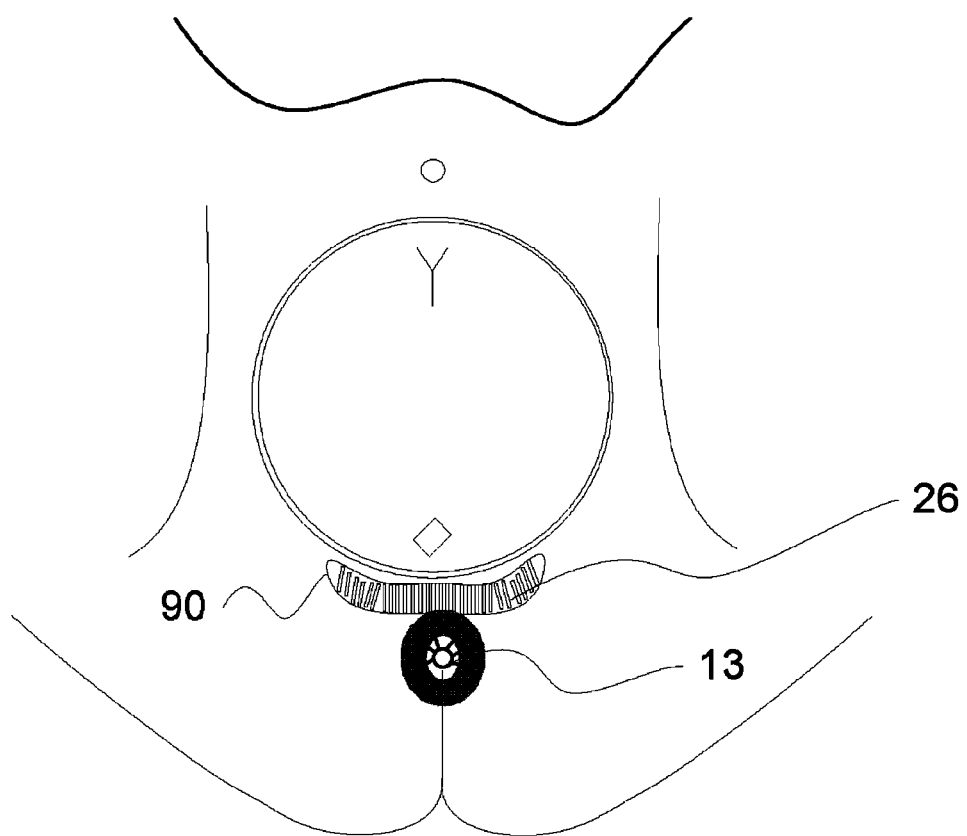
FIG. 15 is a front view of the device of FIG. 14 in use according to an embodiment.

FIG. 15 is a front view of the device 90 in use during childbirth. As may be observed from FIG. 15 the device 90 is in an extended state according to FIG. 14*b*.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A device for reducing tissue damage or ruptures during child delivery, comprising:
   a sheet of flexible material, having an upper side and a lower side, wherein at least a part said lower side in use is in contact with the birth canal wall and the vaginal opening edge and said upper side is faded away from the birth canal wall, wherein said device further comprises
   a lower section to be applied outside the vaginal opening in use, the lower section comprising at least two end sections separated by a slit that extends to an edge of the lower section, thereby facilitating bending of the device at the position of the vaginal opening edge along the vaginal opening edge,
   a middle section connected to the lower section and arranged to be applied to the vaginal opening edge in use,
   a top section connected to the middle section opposite to the lower section, and arranged to be applied to the birth canal wall in use,
   wherein the lower section, the middle section, and the top section divide the device along a longitudinal axis,
   wherein the flexible material of the middle section is continuous between the outermost lateral edges of the device, and
   wherein a distance between the outermost lateral edges of the device at a position of the middle section is larger than a distance between the outermost lateral edges of the device at a position of the top section.

2. The device according to claim 1, wherein said lower side comprises an irregular surface, wherein at least a part of said lower side is configured to provide a friction action between said device and the underlying tissue being in contact with said part of the lower side via said irregular surface.

3. The device according to claim 2, wherein the irregular surface varies over the device.

4. The device according to claims 1, wherein said lower side comprises attachment means for attaching said device to the underlying tissue being in contact with said lower side.

5. The device according to claim 4, wherein said attachment means comprises an adhesive.

6. The device according to claim 4, wherein said attachment means is one of an elastic suture and a clamp.

7. The device according to claim 1, wherein said upper side comprises a surface providing lower friction than that of said lower side.

8. The device according to claim 1, wherein said upper side is provided with a hydrophilic layer.

9. The device according to claim 1, wherein said lower section in use is configured to protect the area around commissura posterior between the vaginal opening and the anal sphincter from rupture or contamination.

10. The device according to claim 1, wherein the lower side comprises at least one of a net structure, a saw-shaped structure, a fish-shell structure, and a suction cup structure.

11. The device according to claim 1, wherein at least a part of said lower side in use is configured to be in contact with the perineal area comprising perineum.

12. The device according to claim 1, wherein each of the at least two end sections comprises an opening.

13. The device according to claim 1, wherein the middle section comprises a flexible material for being able to bend along the edge of the vaginal opening while being in contact with the tissue.

14. The device according to claim 1, wherein the middle section is breakable.

15. The device according to claim 1, wherein said sheet comprises a polymeric material.

16. The device according to claim 1, further comprising a reinforcement member provided at least partly along an axis of said device.

17. The device according to claim 16, wherein said reinforcement member is a reinforcement beam provided at least partly in one of a top section, a middle section, and said lower section of said device.

18. The device according to claim 16, wherein said reinforcement member has a higher stiffness than the stiffness of the flexible material.

19. The device according to claim 1, wherein the sheet comprises a transparent material enabling inspection of underlying tissue during use.

20. The device according to claim 1, wherein the sheet comprises a non-polymeric material.

21. The device according to claim 1, wherein the sheet is configured as one of a plate and a net structure.

22. The device according to claim 1, configured with a combination of different irregular surfaces.

23. The device according to claim 1 having a thickness of 0.1 to 5 mm.

24. The device according to claim 1, wherein the thickness of the sheet varies.

25. The device according to claim 1, wherein said sheet is formed in a U shape.

26. The device according to claim 1, wherein said slit is covered by a stretchable plastic membrane.

27. A device for reducing tissue damage or ruptures during child delivery, comprising:
- a sheet of flexible material, having an upper side and a lower side, wherein at least a part of said lower side in use is arranged to be in contact with the birth canal wall and the vaginal opening edge and said upper side is faced away from the birth canal wall, wherein said device further comprises
- a lower section to be applied outside the vaginal opening in use, the lower section comprising at least two end sections separated by a slit that extends to an edge of the lower section,
- a middle section connected to the lower section and arranged to be applied to the vaginal opening edge in use,
- a top section connected to the middle section opposite to the lower section, and arranged to be applied to the birth canal wall in use,
- wherein the lower section, the middle section, and the top section divide the device along a longitudinal axis,
- wherein the flexible material of the middle section is continuous between the outermost lateral edges of the device, and
- wherein the device when seen from the side in a plane having a normal being parallel to a lateral axis of the device, has a U-shape in an idle state, to which idle state the device strives to return to in use, thereby compressing and holding the underlying tissue together.

28. A device for reducing tissue damage or ruptures during child delivery, comprising:
- a sheet of flexible material, having an upper side and a lower side, wherein at least a part of said lower side in use is arranged to be in contact with the birth canal wall and the vaginal opening edge and said upper side is faced away from the birth canal wall, wherein said device further comprises
- a lower section to be applied outside the vaginal opening in use, the lower section comprising at least two end sections separated by a slit that extends to an edge of the lower section,
- a middle section connected to the lower section and arranged to be applied to the vaginal opening edge in use,
- a top section connected to the middle section opposite to the lower section, and arranged to be applied to the birth canal wall in use,
- wherein the lower section, the middle section, and the top section divide the device along a longitudinal axis,
- wherein the flexible material of the middle section is continuous between the outermost lateral edges of the device, and
- wherein an angle between the top section and the lower section when seen from the side in a plane having a normal being parallel to a lateral axis of the device, is less than 90 degrees in an idle state, to which the device strives to return to in use, thereby compressing and holding the underlying tissue together.

* * * * *